US00RE49667E

(19) United States
(12) Reissued Patent
Fox

(10) Patent Number: US RE49,667 E
(45) Date of Reissued Patent: Sep. 26, 2023

(54) SHAPE CHANGING BONE IMPLANT AND METHOD OF USE FOR ENHANCING HEALING

(71) Applicant: William Casey Fox, Pipe Creek, TX (US)

(72) Inventor: William Casey Fox, Pipe Creek, TX (US)

(21) Appl. No.: 17/506,545

(22) Filed: Oct. 20, 2021

Related U.S. Patent Documents

Reissue of:
(64) Patent No.: 10,448,979
Issued: Oct. 22, 2019
Appl. No.: 14/351,032
PCT Filed: Oct. 10, 2012
PCT No.: PCT/US2012/059603
§ 371 (c)(1),
(2) Date: Apr. 10, 2014
PCT Pub. No.: WO2013/055824
PCT Pub. Date: Apr. 18, 2013

U.S. Applications:
(60) Provisional application No. 61/545,391, filed on Oct. 10, 2011.

(51) Int. Cl.
*A61B 17/72* (2006.01)
*A61B 17/58* (2006.01)
(Continued)

(52) U.S. Cl.
CPC ..... *A61B 17/7291* (2013.01); *A61B 17/0642* (2013.01); *A61B 17/58* (2013.01);
(Continued)

(58) Field of Classification Search
CPC . A61B 17/7291; A61B 17/0642; A61B 17/58; A61B 17/68; A61B 17/8004;
(Continued)

(56) References Cited

U.S. PATENT DOCUMENTS 2,931,038 A 4/1960 Wandel
3,225,996 A 12/1965 Mallina
(Continued)

FOREIGN PATENT DOCUMENTS

WO 2013016633 A1 1/2013

OTHER PUBLICATIONS

Wright Medical; Charlotte Foot and Ankle Fixation System Brochure, SO 040-105 Rev. 04.06 (no month, 2005); Wright Medical Technology, Inc.; US.

(Continued)

*Primary Examiner* — David O Reip
(74) *Attorney, Agent, or Firm* — Dickinson Wright PLLC; Ross Spencer Garsson

(57) ABSTRACT

Described is a new bone healing method and class of bone fixation implants that change shape once implanted so as to minimize non-healing and speed the bone healing process. The bone fixation method involves shape changing implants that continuously hold the bones in apposition so that a gap does not form. Gaps in time allow non-bony tissue to infiltrate and stop healing. Furthermore, the implants actively compress bone to increase bone mass and strength. Bone cell pressure due to compression and electrical current flow due to bone deformation act to stimulate healing. The new implant designs also provide a scaffolding to conduct bone through the implant and across the healing bone interface. The methods and designs are applicable to but not limited to use for bone screws, plates, staples, rods, cylinders and external fixation devices.

31 Claims, 13 Drawing Sheets

(51) Int. Cl.
*A61B 17/064* (2006.01)
*A61B 17/86* (2006.01)
*A61B 17/80* (2006.01)
*A61B 17/84* (2006.01)
*A61B 17/00* (2006.01)

(52) U.S. Cl.
CPC ..... *A61B 17/8004* (2013.01); *A61B 17/8061* (2013.01); *A61B 17/844* (2013.01); *A61B 17/866* (2013.01); *A61B 17/8695* (2013.01); *A61B 2017/00867* (2013.01)

(58) Field of Classification Search
CPC . A61B 17/8061; A61B 17/844; A61B 17/866; A61B 17/8695; A61B 17/725; A61B 17/7258; A61B 17/7275; A61B 17/7283
See application file for complete search history.

(56) References Cited

U.S. PATENT DOCUMENTS 3,939,828 A * 2/1976 Mohr ..... A61B 17/68 606/221
3,960,147 A 6/1976 Murray
3,986,504 A * 10/1976 Avila ..... A61B 17/7266 606/63
4,262,665 A * 4/1981 Roalstad ..... A61B 17/7225 606/62
4,414,967 A 11/1983 Shapiro
4,415,111 A 11/1983 McHarrie et al.
4,438,769 A 3/1984 Pratt et al.
4,444,181 A * 4/1984 Wevers ..... A61B 17/0642 606/75
4,527,726 A 7/1985 Assei et al.
4,540,110 A 9/1985 Bent et al.
4,665,906 A 5/1987 Jervis
4,741,336 A 5/1988 Failla et al.
4,790,304 A * 12/1988 Rosenberg ..... A61B 17/7291 606/302
4,841,960 A * 6/1989 Garner ..... A61B 17/0642 606/216
5,067,957 A 11/1991 Jervis
5,246,443 A 9/1993 Mai
5,449,359 A * 9/1995 Groiso ..... A61B 17/0642 411/459
5,474,557 A 12/1995 Mai
5,779,707 A 7/1998 Berlolet et al.
5,853,414 A 12/1998 Groiso
6,001,110 A * 12/1999 Adams ..... A61B 17/122 606/151
6,059,787 A * 5/2000 Allen ..... A61B 17/0642 606/75
6,193,733 B1 2/2001 Adams
6,268,589 B1 7/2001 Flot
6,323,461 B2 11/2001 Flot
6,325,805 B1 12/2001 Ogilvie et al.
6,348,054 B1 2/2002 Allen
6,530,933 B1 3/2003 Yeung et al.
6,575,973 B1 * 6/2003 Shekalim ..... A61B 17/7266 606/62
6,685,708 B2 2/2004 Monassevitch et al.
6,767,350 B1 * 7/2004 Lob ..... A61B 17/68 606/326
6,773,437 B2 8/2004 Ogilvie et al.
6,783,531 B2 8/2004 Allen
7,240,677 B2 7/2007 Fox
7,556,647 B2 7/2009 Drews et al.
7,618,441 B2 11/2009 Groiso
7,635,367 B2 12/2009 Groiso
7,828,189 B2 11/2010 Holsten et al.
8,596,514 B2 12/2013 Miller et al.
9,138,274 B1 * 9/2015 Biesinger ..... A61B 17/844
9,545,274 B2 * 1/2017 McCormick ..... A61B 17/7291
2002/0068939 A1 * 6/2002 Levy ..... A61B 17/7258 606/63
2002/0173793 A1 11/2002 Allen
2003/0130660 A1 * 7/2003 Levy ..... A61B 17/7266 606/63
2004/0230193 A1 * 11/2004 Cheung ..... A61B 17/7266 606/63
2005/0055027 A1 3/2005 Yeung et al.
2005/0273108 A1 * 12/2005 Groiso ..... A61B 17/0642 606/75
2006/0058796 A1 * 3/2006 Hartdegen ..... A61B 17/1728 606/281
2006/0142771 A1 * 6/2006 Beutter ..... A61B 17/0642 606/75
2006/0264950 A1 * 11/2006 Nelson ..... A61B 17/7208 606/916
2006/0271061 A1 * 11/2006 Beyar ..... A61B 1/00071 606/105
2007/0067034 A1 * 3/2007 Chirico ..... A61B 17/70 623/17.11
2007/0093839 A1 * 4/2007 Beckendorf ..... A61B 17/0642 606/75
2007/0104978 A1 * 5/2007 Che ..... C07F 15/0033 428/690
2007/0270855 A1 * 11/2007 Partin ..... A61B 17/7225 606/279
2008/0082124 A1 4/2008 Hess et al.
2008/0161808 A1 * 7/2008 Fox ..... A61B 17/0642 606/75
2008/0177262 A1 * 7/2008 Augoyard ..... A61B 17/68 606/70
2009/0005782 A1 * 1/2009 Chirico ..... A61B 17/1617 606/63
2010/0023062 A1 1/2010 Faillace et al.
2010/0036430 A1 2/2010 Harldegen et al.
2010/0125275 A1 * 5/2010 Kinmon ..... A61B 17/0642 606/75
2010/0131014 A1 * 5/2010 Peyrot ..... A61F 2/30 606/300
2010/0193569 A1 8/2010 Yates et al.
2011/0144644 A1 * 6/2011 Prandi ..... A61B 17/68 606/62
2011/0144766 A1 * 6/2011 Kale ..... A61B 17/686 623/23.63
2011/0301653 A1 * 12/2011 Reed ..... A61B 17/1604 606/319
2011/0319946 A1 * 12/2011 Levy ..... A61B 17/7035 606/309
2013/0090655 A1 * 4/2013 Tontz ..... A61B 17/7233 606/64
2014/0257420 A1 * 9/2014 Fox ..... A61B 17/0642 606/86 R
2015/0073413 A1 * 3/2015 Palmer ..... A61B 17/7266 606/63
2015/0223849 A1 * 8/2015 McCormick ..... A61B 17/7291 606/63
2016/0317198 A1 * 11/2016 Fox ..... A61B 17/225

OTHER PUBLICATIONS

Biopro, Inc.; The BioPro Memory Staple Brochure, Brochure No. 17704, rev. 2, (May 2010); BioPro; US.
Depuy Orthopaedics, Inc.; Memory Staple Brochure, Brochure 0612-00-584 (Rev. 1) (no month, 2006); DePuy Orthopaedics, Inc.; US.
MMI-USA, Easy Clip SI SuperElastic Fixation System Brochure, ECLP1000-rev D (Aug. 12, 2009), Memometal Inc., a Memometal Technologies, Inc.; US.
Biomedical Enterprises, Inc.; OSStaple Brochure, Brochure No. A108-076 (Rev B); (No Month 2010); BioMedical Enterprises, Inc.; US
Patent Cooperation Treaty; PCT International Search Report, Issued in connection with PCT/US2012/048539; dated Oct. 18, 2012; 4 pages; US.
Patent Cooperation Treaty; PCT Written Opinion of the International Searching Authority, Issued in connection with PCT/US2012/048539; dated Oct. 18, 2012; 19 pages; US.

(56) References Cited

OTHER PUBLICATIONS

S.J. Warden et al.; Mechanotransduction in cortical bone is most efficient at loading frequences of 5-10 Hz; Nov. 7, 2003; pp. 261-270; Elsevier Inc.; US.
C.H. Turner et al.; Basic Biomechanical Measurements of Bone: A Tutorial; (no month, 1993); pp. 595-608; Pergamon Press Ltd.; US.
Clinton T. Rubin et al.; Regulation of Bone Mass by Mechanical Strain Magnitude; (no month, 1985); pp. 411-417; Calcified Tissue International; US.
Alexander G. Robling et al.; Biomechanical and Molecular Regulation of Bone Remodeling; Apr. 3, 2006; pp. 455-498; The Annual Review of Biomedical Engineering; US.
Rich Lipschutz et al.; 510K Summary of Safety and Effectiveness, Fx Devices POGO Screw; Oct. 10, 2008; 5 pages; US.
Edmund Y.S. Chao et al.; Biophysical Stimulation of Bone Fracture Repair, Regeneration and Remodelling; (no month, 2003); pp. 72-85; vol. 6; European Cells and Materials; US.
A. Chamay et al.; Mechanical Influences in Bone Remodeling, Experimental Research on Wolff's Law; (no month, 1972); pp. 172-180; vol. 5; J. Biomechanics; Great Britain.

* cited by examiner

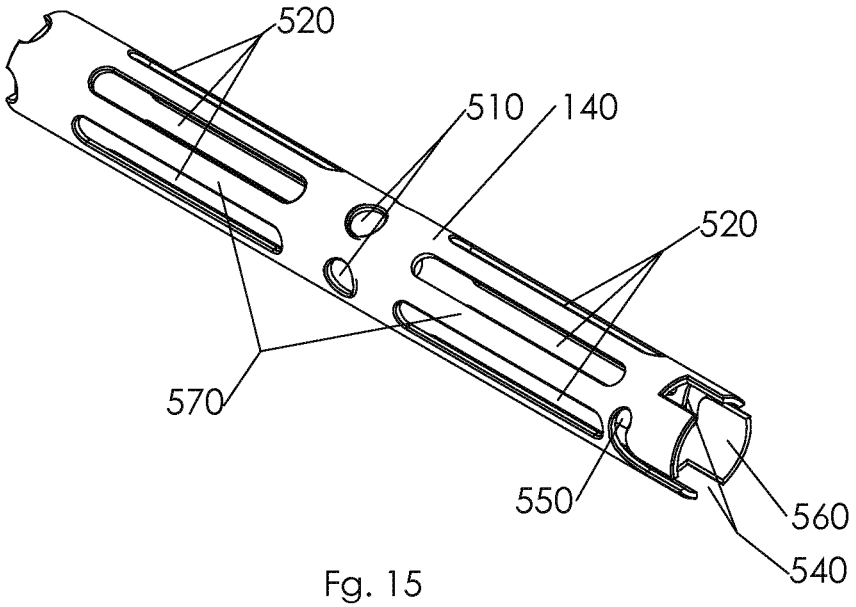
Fg. 15
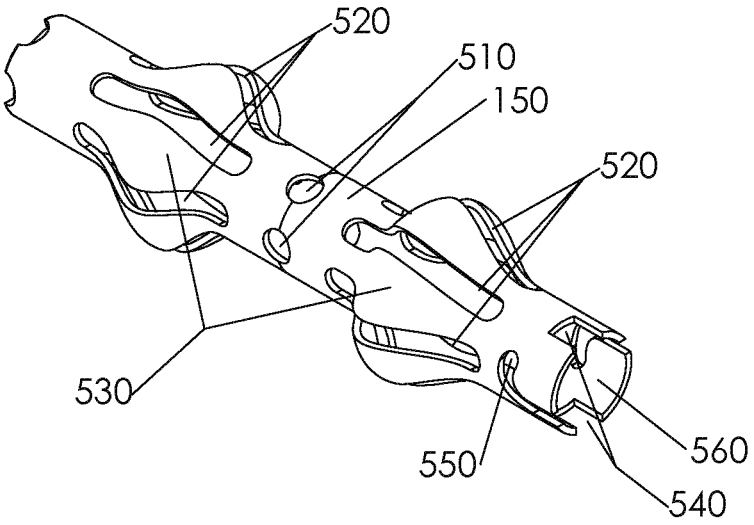
Fig. 16

SHAPE CHANGING BONE IMPLANT AND METHOD OF USE FOR ENHANCING HEALING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED PATENT APPLICATIONS

This Application *a reissue application of U.S. Pat. No. 10,448,979, entitled "Shape Changing Bone Implant And Method Of Use For Enhancing Healing," which issued on Oct. 22, 2019, from U.S. patent application Ser. No. 14/351,032, filed Apr. 10, 2014, which* is the 35 U.S.C. § 371 national application of International Patent Application No. PCT/US2012/059603, entitled "Shape Changing Bone Implant And Method Of Use For Enhancing Same," filed Oct. 10, 2012, which designated the United States and claimed priority to U.S. Patent Appl. Ser. No. 61/545,391, entitled "Bone Healing Devices and Methods For Making and Using Thereof," filed on Oct. 10, 2011. [Both of these] *These* patent applications are commonly owned by the owner of the present invention.

This Application is related to: (a) U.S. patent application Ser. No. 13/192,162; (b) U.S. patent application Ser. No. 13/192,177; (c) U.S. patent application Ser. No. 13/192,186; and (d) U.S. patent application Ser. No. 13/192,198. Each of the foregoing patent applications were filed on Jul. 27, 2011, are entitled "Bone Staple, Instrument and Method of Use And Manufacturing," and are commonly owned by the owner of the present invention.

This Application is also related to International Patent Appl. No. PCT/US2012/048539, entitled "Bone Staple, Instrument and Method of Use And Manufacturing," filed on Jul. 27, 2012, and is commonly owned by the owner of the present invention.

The foregoing patent applications are hereby incorporated herein by reference in their entirety for all purposes.

TECHNICAL FIELD

This application relates to promoting bone healing with a new class of shape changing bone implants used for fixation of the musculoskeletal system. Bone healing is promoted because the implants change shape to constantly hold the healing interface of bone segments in apposition while compressing. The implants change shape through their metallurgic (or polymeric) properties and mechanisms to use mechanically stored strain energy pull together and compresses bone to induced an enhanced healing response. These implants can also act as a scaffolding for bone thus conducting bone formation through the implant during the healing process.

BACKGROUND

Bone wires, screws, staples, rods, plates, and combinations of these devices have been in clinical use for decades. These bone fixation devices have evolved from industrial designs for fastening wood, steel, plastic or other materials. The use of these types of devices for bone fixation and the formation of a rigid construct of bone and implant are the basis of current skeletal fixation technology to support healing and functional repair.

In spite of this prior art rigid internal fixation implant technology, bone healing and repair often does not occur. In these circumstances, fractures may not heal and bone cuts or diseased joints may not fuse. This delayed- or non-healing response occurs because the bones are too far apart, unwanted motion occurs, soft tissue fills the space between the healing bones, or the biologic response to healing is poor (which can be due to a host of factors, including age, systemic disease, infection, diet, or smoking).

Rigid bone implants are commonly hammered, wedged, screwed, or fixed with wire into bone. Surgical techniques involve alignment of the bone segments, approximating the edges where healing should occur, and using implants to rigidly hold the bones in place.

The first phase of bone healing is inflammation. This normal response recruits cells into the wound to remove debris including necrotic tissue. In this process the bone edges that were surgically approximated are broken down by tissue digesting cells causing gaps between the bone edges to form. These gaps, caused by difficult surgical reduction and/or inflammation mediated bone resorbtion, delay healing because more bone tissue must form to fill the gaps and bone healing may stop if soft tissue infiltrates the gaps and impedes or blocks bone fusion.

Until recently, all known implants were rigid constructs. Nitinol bone staples described in patents/patent applications of the Applicant (Fox '677 Patent, Fox '808 Application, Fox '506 Application), as well as other related patents (Jervis '957 Patent, Mai '443 Patent, Mai '557 Patent, Groiso '359 Patent, Groiso '414 Patent, Groiso '367 Patent, Bertolet '707 Patent, Allen '787 Patent, Allen '054 Patent, Allen '531 Patent, Flot '805 Patent, Flot '461 Patent, Ogilvie '805 Patent) along with non-nitinol staples (Mohr '828 Patent), were the first bone fixation implants that changed or were caused to change shape to fasten bone.

Some of these devices are presently on the market such as those illustrated in BioMedical Enterprises's Product Sell Sheet. Other companies, such as MBA (France), used the technology described and taught in Flot '589 Patent and Flot '461 Patent, which used electrical current to heat the staple. These two commercial technologies caused these nitinol staples to change shape when heated but had little, and depending on implantation technique, often no continued shape change when healing.

Memometal, Inc.'s (now Stryker Corp. (Kalamazoo, Mich.)) EasyClip™ staples and BioMedical Enterprises, Inc.'s Speed™ staples are nitinol staples that spring back but use a non-contracting straight bridge and consequently can not pull the two bone segments any closer together than the spacing of the original two drill holes.

Biopro's Memory Staple Brochure and Depuy's Memory Staple Brochure both show a nitinol staple that changes shape at body temperature hours following the operative procedure. These staples are changing shape when implanted so are inconsistently implanted. They create bone fixation force when the wound is closed, sometimes creating complications, such as fracture or malalignment.

Other devices, such as the FxDevices' Pogo® screw described in Tipirneni '026 Application, Tipirneni '248 Application, and Tipirneni '127 Application, US2007/0162026 and FDA K080649 Clearance to Market Letter, use internal features such as moving parts and springs to create compression. Patents to which the Applicant is the inventor (Fox '351 Patent, Fox '310 Patent) also include internal mechanisms to change the shape of the implant to conform to the bone defect into which they are placed. These devices provide bone compression at the edges of a hole, and, in the experimental use of implants fabricated using the technology of Fox '351 Patent and Fox '310 Patent, they were shown to cause the bone being compressed by the implant to become more dense in structure and presumably stronger.

Though Fox '351 Patent and Fox '310 Patent is the first work known to the Applicant of an implant compressing bone that results in increases in bone density. Historically the research literature on the effects of the mechanical loading of intact bone is well known and referred to as Wolff's Law. Wolff's law is a theory developed by Julius Wolff (1836-1902) that states that bone in a healthy person will adapt to the loads it is placed under. If loading on a bone increases, that bone will remodel itself over time to become stronger to resist that the loading. Conversely, if the loading on the bone decreases, it will become weaker as there is no stimulus for the continued remodeling (which is required to maintain bone mass).

Wolff's Law has resulted in a clinical recommendation to exercise to delay osteoporosis or bone loss in the weightlessness of outer space. Like muscle, exercise that mechanically loads bone also seems to increase the bone size and strength. This phenomena associated with Wolff's Law is known as mechanotransduction.

Studies of mechanotransduction are replete in the literature involving space flight, bed rest, functional loading and remodeling, and have been published by many, including, but not limited to: Chama 1972, Chama 1972, Turner 1993, Robling 2006, Warden 2004, and Rubin 1985. However, no theory or understanding has been presented on the enhancement of bone healing with implants that change shape to pull together and compress the healing bone interface.

Chamay 1972 reported about compression induced microlesions and a bone formation and hypertrophy response in three different test groups. They studied three loading conditions: (1) a dynamic fatigue test group, (2) a static overload group, and (3) single load group, and showed that each resulted in various degrees, locations, and timing of new bone formation.

Chao 2003 stated that, though it has long been hypothesized that that there is a link between mechanical stimulation and fracture healing, the biologic pathways and regulating cellular mechanisms remain unknown. Chao 2003 further stated that when the mechanisms at the cellular levels became understood, physiological conditions or pharmacological agents may be developed to enhance bone healing.

These studies of mechanotransduction have been focused on the remodeling of intact bone to impede osteoporosis and though effects on bone fracture healing have been hypothized no method, device, substance, or research has been proposed to enhance fracture healing.

SUMMARY OF THE INVENTION

The embodiments of the subject invention describe an improved bone implant that stores recoverable mechanical energy in its structure or mechanism and changes shape to pull together and compress the bone fixation interface. This is a new class of implant that not only compresses but can translate bone segments to hold them into constant apposition which has multiple advantages over prior bone fixation devices that are rigid. This invention further describes a method of manipulating bone to promote healing and minimize non-healing events by holding the bone edges in constant contact and applying pressure to the healing interface to promote a biologic response to form bone. This method is further enhanced by implants that can act as a scaffolding for bone, thus conducting bone formation through the implant so as to fuse the bone segments.

In general, in one aspect, the invention features a bone healing method that includes selecting a bone implant operable for pulling together a first bone segment and a second bone segment and operable for compressing the first bone segment and the second bone segment at a bone healing interface. The method further includes positioning the bone implant in a position to pull the first bone segment and the second bone segment together and to compress the first bone segment and the second bone segment at the bone healing interface. During the step of positioning in the method, the bone implant applies no mechanical force to pull the first bone segment and the second bone segment together. During the step of positioning in the method, the bone implant applies no mechanical force to compress the first bone segment and the second bone segment at the bone healing interface. The method further comprises that, after positioning of the bone implant, mechanically activating the bone implant. The mechanically activated bone implant pulls together the first segment and the second bone segment. The mechanically activated bone implant compresses the first bone segment and the second bone segment at the bone healing interface. The mechanically activated bone implant maintains the first bone segment and the second bone segment at the bone healing interface while the first bone segment and the second bone segment heal.

Implementations of the invention can include one or more of the following features:

The bone implant can be a cage, wire, staple, plate, screw, rod, tubular structure, external fixation device, or a combination thereof.

The bone implant can have a first shape. The first shape can be an expanded shape. The bone implant can be in the first shape during the step of positioning.

The bone implant can have a second shape. The second shape can be a contracted shape. The bone implant can move from the first shape toward the second shape during or after the step of mechanically activating the bone implant.

The bone implant can have a first shape change in first direction and a second shape change in another direction. The first shape change and the second shape change can be different. The first shape change can be a shape expansion or contraction. The second shape change can be a shape expansion or contraction.

The bone implant can change to a different shape during or after the step of mechanically activating the bone implant.

The transition of the bone implant to the different shape can be operable for pulling together the first bone segment and the second bone segment. The transition of the bone implant to the different shape can be operable for compressing the first bone segment and the second bone segment at the bone healing interface.

The bone implant can include nitinol.

The bone implant can include an activator. Before the activator is removed from the bone implant, the activator can retain the bone implant in a first shape in which at least some of the nitinol in the bone implant is in the form of stress induced or retained martensite. The activator can be removed from the bone implant during the step of mechanically activated bone implant. After the activator is removed from the bone implant, the bone implant can change shape, during which at least some of the nitinol in the bone implant can change in form to austenite.

The bone healing implant can include a shape memory metal, an elastic biocompatible metal, an elastic biocompatible polymer, or a combination thereof.

The bone healing implant can include stainless steel, titanium, or a combination thereof.

The bone healing implant can include comprises polyether ether ketone (PEEK), polyethylene, or a combination thereof.

The bone implant can include a spring. The spring can be released during the step of mechanical activating the bone implant. The spring can provide the mechanical force that pulls together the first bone segment and the second bone segment. The spring can provide the mechanical force that compresses the first bone segment and a second bone segment at the bone healing interface. The spring can provide the mechanical force that maintains the bone under compression while the bone heals.

The bone implant can include nitinol. Before the spring is released, the spring can hold the bone implant in a shape in which at least some of the nitinol in the bone implant is in the form of martensite. The bone implant can hold together the first bone segment and the second bone segment such that soft tissue infiltration is blocked.

The bone implant can deform the first bone segment and the second bone segment so as to create an electrical current flow in the first bone segment and the second bone segment.

The bone implant can include a shape changing cage.

The shape changing cage can include at least one bone conducting scaffold feature.

The shape changing cage can include a first component, a second component, and a spring.

During the step of mechanical activation of the method, a locking pin can be removed from the bone implant. During the step of mechanical activation of the method, the first component and the second component can be pulled together. The pulling together of the first component and the second component can pulls together the first bone segment and the second bone segment. The pulling together of the first component and the second component can compress. the first bone segment and the second bone segment at the bone healing interface. The pulling together of the first component and the second component can maintain the first bone segment and the second bone segment at the bone healing interface while the first bone segment and the second bone segment heal.

The shape changing cage can include nitinol.

The shape changing cage can include a shape memory metal, an elastic biocompatible metal, an elastic biocompatible polymer, or a combination thereof.

The shape changing cage can include stainless steel, titanium, or a combination thereof.

The shape changing cage can include polyether ether ketone (PEEK), polyethylene, or a combination thereof.

The shape changing cage can include a first cylindrical component and a second cylindrical component. The first cylindrical component and second cylindrical component can be locked in place to prevent them from moving together.

The bone implant can further include a mandrel that locks the shape changing cage in a first shape.

The mandrel can include a bone cutting insertion tip that is used during the step of positioning the bone implant.

The step of mechanically activating the bone implant in the method can include unlocking the cage by removing the mandrel from the implant. Unlocking the cage can allow the cage to change its shape. The change in shape of the cage can pull together the first segment and the second bone segment. The change in shape of the cage can compress the first bone segment and the second bone segment at the bone healing interface. The change in shape of the cage can maintain the first bone segment and the second bone segment at the bone healing interface while the first bone segment and the second bone segment heal.

The shape changing cage can include nitinol.

The shape changing cage can include a shape memory metal, an elastic biocompatible metal, an elastic biocompatible polymer, or a combination thereof.

The shape changing cage can include stainless steel, titanium, or a combination thereof.

The shape changing cage can include polyether ether ketone (PEEK), polyethylene, or a combination thereof.

In general, in another aspect, the invention features a bone implant that includes a biocompatible material structure that is in a first shape. The first shape allows the section to be positioned proximate to a first bone segment and a second bone segment without the biocompatible material structure applying mechanical forces to pull together the first bone segment and the second bone segment. The first shape allows the section to be positioned proximate to a first bone segment and a second bone segment without the biocompatible material structure applying mechanical forces to compress the first bone segment and the second bone segment at a bone healing interface. The bone implant further includes an actuator holding the biocompatible material structure in the first shape. The biocompatible material structure is operable to move toward a second shape upon actuation of the actuator. The movement of the biocompatible material structure toward the second shape is operable to pull together the first segment and the second bone segment. The movement of the biocompatible material structure toward the second shape is operable to compress the first bone segment and the second bone segment at the bone healing interface. The movement of the biocompatible material structure to the second shape is operable to maintain the first bone segment and the second bone segment at the bone healing interface while the first bone segment and the second bone segment heal.

Implementations of the invention can include one or more of the following features:

The biocompatible material structure can include at least one bone conducting scaffold feature.

The biocompatible material structure can be a cage, wire, staple, plate, screw, rod, tubular structure, external fixation device, or a combination thereof.

The first shape can be an expanded shape.

The second shape can be a contracted shape.

The first shape can be a contracted shape.

The second shape can be an expanded shape.

The biocompatible material structure can include nitinol.

At least some of the nitinol in the biocompatible material structure can be in the form of stress induced or retained martensite when the biocompatible material structure is in the first shape. At least some of the nitinol can be operable for changing in form from martensite to austenite due to change in the biocompatible material structure from the first shape toward the second shape.

The bone healing implant can include a shape memory metal, an elastic biocompatible metal, an elastic biocompatible polymer, or a combination thereof.

The bone healing implant can include stainless steel, titanium, or a combination thereof.

The bone healing implant can include polyether ether ketone (PEEK), polyethylene, or a combination thereof.

The bone implant can further include a spring. The spring can be operatively connected to the biocompatible material structure and the actuator such that actuation of the actuator is operable for releasing of the spring. The spring can be operatively connected to the biocompatible material structure and the actuator such that releasing of the spring is operable for releasing the biocompatible material structure such that the biocompatible material structure can change from the first shape toward the second shape.

The biocompatible material structure can include nitinol.

The biocompatible material structure can include a shape memory metal, an elastic biocompatible metal, an elastic biocompatible polymer, or a combination thereof.

The shape changing cage can include stainless steel, titanium, or a combination thereof.

The shape changing cage can include polyether ether ketone (PEEK), polyethylene, or a combination thereof.

The movement of the biocompatible material structure toward the second shape can be operable to compress the first bone segment and the second bone segment at the bone healing interface to block soft tissue infiltration.

The movement of the biocompatible material structure toward the second shape can be operable to deform the first bone segment and the second bone segment so as to create an electrical current flow in the first bone segment and the second bone segment.

The biocompatible material structure can include a shape changing cage.

The shape changing cage can include at least one bone conducting scaffold feature.

The shape changing cage can include a first component and a second component. The bone implant can further include a spring. The spring can be operable to maintain the first component and the second component so that the shape changing cage is in the first shape. The spring can be operable to be released by the actuation of the actuator. The first component and the second component can be operable to pull together, upon release of the spring, to move the shape changing cage toward the second shape.

The activator can be a plate, tong, clip, wire, rod, or a combination thereof.

The activator can be a locking pin.

The first component and the second component can be operable for pulling together when the locking pin is removed from the bone implant. The pulling together of the first component and the second component can be operable for pulling together the first bone segment and the second bone segment. The pulling together of the first component and the second component can be operable for compressing the first bone segment and the second bone segment at the bone healing interface. The pulling together of the first component and the second component can be operable for maintaining the first bone segment and the second bone segment at the bone healing interface while the first bone segment and the second bone segment heal.

The biocompatible material structure can include nitinol.

The biocompatible material structure can include a shape memory metal, an elastic biocompatible metal, an elastic biocompatible polymer, or a combination thereof.

The biocompatible material structure can include stainless steel, titanium, or a combination thereof.

The biocompatible material structure can include polyether ether ketone (PEEK), polyethylene, or a combination thereof.

The shape changing cage can include a first component and a second component. The first component and the second component can be locked in place by the actuator. The first component and the second component can be operable for pulling toward each other upon actuation of the actuator.

The actuator can be a mandrel that locks the cage in the first shape.

The mandrel can include a bone cutting insertion tip.

The actuator can be operable for removal from the shape changing cage to allow the shape changing cage to change its shape from the first position toward the second position.

The shape changing cage can include nitinol.

The shape changing cage can include a shape memory metal, an elastic biocompatible metal, an elastic biocompatible polymer, or a combination thereof.

The shape changing cage can include stainless steel, titanium, or a combination thereof.

The shape changing cage can include polyether ether ketone (PEEK), polyethylene, or a combinations thereof.

In general, in another aspect, the invention features a bone healing implant that includes a shape changing washer and a threaded bone screw. The shape changing washer and the threaded bone screw are operable for use to pull together a first bone segment and a segment bone segment. The shape changing washer is operable for storing mechanical energy by changing its shape as the threaded bone screw is rotated when used to pull together the first bone segment and the segment bone segment. The stored mechanical energy of the shape changing washer is operable to pull together the first bone segment and a second bone segment. The stored mechanical energy of the shape changing washer is operable to compress the first bone segment and the second bone segment at the bone healing interface. The movement of the biocompatible material structure to the second shape is operable to maintain the first bone segment and the second bone segment at the bone healing interface while the first bone segment and the second bone segment heal.

Implementations of the invention can include one or more of the following features:

The shape changing washer can have changing bellows.

The bone healing implant can further include at least one bone conducting scaffold feature.

The shape changing washer can include nitinol.

The shape changing washer can include a shape memory metal, an elastic biocompatible metal, an elastic biocompatible polymer, or a combination thereof.

The shape changing washer can include stainless steel, titanium, or a combination thereof.

The shape changing washer can include polyether ether ketone (PEEK), polyethylene, or combination thereof.

In general, in another aspect, the invention features a bone healing method that includes selecting a bone implant. The bone implant has at least one bone scaffold feature. The method further includes positioning the bone implant in a position to pull first bone segment and a second bone segment together and to compress the first bone segment and the second bone segment at the bone healing interface. When so positioned in the method, the bone implant pulls together the first segment and the second bone segment. When so positioned in the method, the bone implant compresses the first bone segment and the second bone segment at the bone healing interface. When so positioned in the method, the bone implant maintains the first bone segment and the second bone segment at the bone healing interface while the first bone segment and the second bone segment heal. The bone scaffold feature conducts bone through the bone implant and across the healing bone interface utilizes while the first bone segment and the second bone segment heal.

Implementations of the invention can include one or more of the following features:

The bone scaffold feature can be a fenestration for bone ingrowth.

The bone scaffold feature can be a circular fenestration for bone ingrowth, an elongated fenestration for bone growth, a slot fenestration for bone growth, a lumen for bone ingrowth, or a combination thereof.

The bone scaffold feature can be a shape changing feature.

The bone implant can include nitinol.

The bone implant can include a shape memory metal, an elastic biocompatible metal, an elastic biocompatible polymer, or a combination thereof.

The bone implant can include stainless steel, titanium, or a combination thereof.

The bone implant can include polyether ether ketone (PEEK), polyethylene, or a combination thereof.

In general, in another aspect, the invention features a bone implant that includes biocompatible material structure that is in a first shape. The first shape allows the biocompatible material structure to be positioned proximate to a first bone segment and a second bone segment. The biocompatible material structure is operable to move from a first shape to a second shape. Movement of the biocompatible material structure toward the second shape is operable to pull together the first segment and the second bone segment. Movement of the biocompatible material structure toward the second shape is operable to compress the first bone segment and the second bone segment at the bone healing interface. Movement of the biocompatible material structure to the second shape is operable to maintain the first bone segment and the second bone segment at the bone healing interface while the first bone segment and the second bone segment heal. The bone implant further includes at least one bone scaffold feature incorporated with the biocompatible material structure. The bone scaffold feature is operable to conduct bone through the implant and across the healing bone interface while the first bone segment and second bone segment heal.

Implementations of the invention can include one or more of the following features:

The bone scaffold feature can be a fenestration for bone ingrowth.

The bone scaffold feature can be a circular fenestration for bone ingrowth, an elongated fenestration for bone growth, a slot fenestration for bone growth, a lumen for bone ingrowth, or a combination thereof.

The bone scaffold feature can be a shape changing feature.

The biocompatible material structure can include nitinol.

The biocompatible material structure can include a shape memory metal, an elastic biocompatible metal, an elastic biocompatible polymer, or a combination thereof.

The biocompatible material structure can include stainless steel, titanium, or a combination thereof.

The biocompatible material structure can include polyether ether ketone (PEEK), polyethylene, or a combination thereof.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DESCRIPTION OF DRAWINGS

FIG. 15 illustrates an orthogonal view of a bone fixation cylindrical cage of FIG. 13 in its elongated and diametrically contracted pre-implantation condition with bone ingrowth fenestrations and holes, and elongated ribs storing maximum mechanical strain energy.

FIG. 16 illustrates an orthogonal view of the bone fixation cylindrical cage of FIG. 14 in its shortened and expanded post-implantation condition with bulging ribs and no stored mechanical strain energy.

REFERENCE NUMERALS

Figure 1:
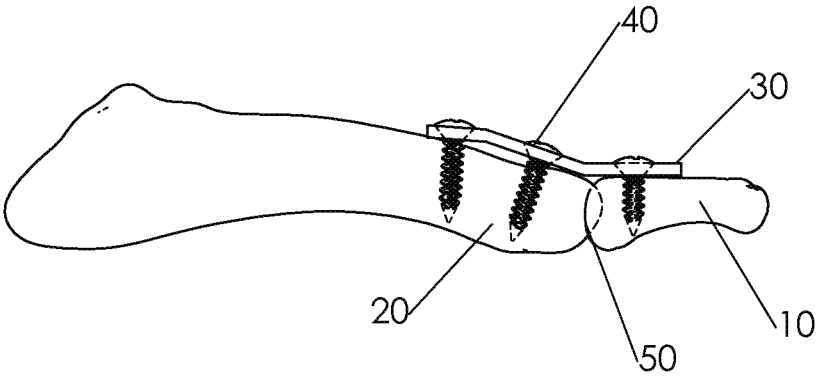
FIG. 1 illustrates a rigid bone fixation plate and screw system of the prior art.

10 First bone segment.
20 Second bone segment.
30 Rigid bone plate.
40 Rigid bone plate screws.
50 Bone healing junction between the first bone segment and second bone segment being held in contact.
60 Inflammation, motion or procedure induced bone gap with non-bony tissue interpositioned between the first bone segment and second bone segment.
62 Bone healing interface of second bone segment 20.
64 Bone healing interface of first bone segment 10.
70 Shape changing element of a contracting bone plate 90 in its unstable uncontracted state.
80 Shape changing element of a contracting bone plate 90 in its contracted state.
90 Shape changing bone plate that can exist in a contracted, extended or intermediate state.
100 Shape changing staple in its unstable uncontracted state in which it stores mechanical energy and is in a condition to pull together and compress the bone segments 10 and 20 so as to continuously close the gap 60.
110 Shape changing bone staple in its contracted state in which its bridge has shortened and its legs have deflected inwards.
120 Shape changing cylindrical fenestrated hollow cylinder in its extended length and contracted diameter with internal springs.
130 Shape changing cylindrical fenestrated hollow cylinder in its contracted length and expanded diameter.
140 Shape changing cylindrical fenestrated hollow cage in its extended length and contracted diameter unstable state that uses its material properties to change shape.
150 Shape changing cylindrical fenestrated hollow cylinder in its contracted length and expanded diameter using its material properties to change shape.
153 Cage implantation mandrel for a shape changing cylindrical fenestrated hollow cylinder.
155 Cage implantation mandrel retention lobe.
156 Bone cutting insertion tip of insertion mandrel 153.
160 Bone screw configured to operate with a shape changing washer.
170 Shape changing washer in its unstable state ready to change shape with maximum stored elastic energy.
180 Shape changing washer in a partially deflected state pulling on the bone screw
160 and compressing bone as the interface gap 50 is held in apposition.
185 Shape changing washer with no stored elastic energy.
190 Movably connected expansion member for cylindrical fenestrated cylindrical cage.
200 Circular fenestrations for bone ingrowth.
210 Elongated fenestrations for bone ingrowth.
220 Mechanical energy storage and shape change spring.
230 Movably connected expansion member actuator.
240 Shape changing cylindrical internal locking fenestration.
250 Fenestration mechanism lock pin.
260 Lock pin manipulator.
270 Lock pin receiver.
280 First half of shape changing cylindrical cage.
290 Second half of shape changing cylindrical cage.
400 Alternate embodiment of a shape changing washer.
410 Alternate embodiment washer 400 with shape changing section elongated and storing mechanical elastic strain energy.
420 Alternate embodiment washer 400 with shape changing section contracted and not storing mechanical elastic strain energy.
510 Circular fenestrations of the alternate embodiment for bone ingrowth.
520 Slot fenestrations of the alternate embodiment for bone ingrowth.
530 Expanded ribs of the fenestrated cylinder.
540 Instrument driving fenestrations.
550 Instrument release fenestrations.
560 Shape changing bone fixation cylinder lumen for bone ingrowth.
570 Straight ribs of the fenestrated cylinder storing maximum shape changing energy.

DETAILED DESCRIPTION

The invention consist of a method of enhancing bone healing by actively pulling the bone segments together at the healing interface and squeezing so as to continuously hold the bones in contact and create mechanical stress in the bone. The invention further includes bone fixation implants that change shape to implement this method. The enhanced bone healing due to mechanical shape change is further advanced through embodiments of the implant invention that conduct bone healing through fenestrations and its lumen. Bone fixation shape changing implant designs that use this method include screws, washers, cylindrical cages, plates, staples, rods, and external fixators.

Since around 2000, Applicant has observed surgical procedures and the bone healing outcome when the OSStaple™ implant (Applicant's invention disclosed and taught in Fox '677 Patent) was implanted to fixate bone fracture and fusions. In such observations by Applicant (and confirmed by direct discussions with clinicians performing the procedures observed), unexpected results were observed and it was seen that (1) the OSStaple™ implant changed shape in bone with time, (2) the bone cut "osteotomy" or fracture was not visible on x-ray at an earlier time-point in healing, (3) the bone healed through primary bone healing (i.e., without a callus and just direct fusion with normal anatomy), not secondary bone healing (i.e., with a callus and bulbous anatomy at the fusion site), (4) that healing occurred quicker, and (5) non-healing occurred less frequently.

These remarkable observations were unexpected and upon further study two conditions were observed that illustrated the mechanism through which healing was enhanced. One mechanism was that the implant's shape change closed bony gaps, which mechanically blocked soft tissue infiltration between the bone segments. A second mechanism was that the implant's mechanical loading of bone played to Wolff's Law and stimulated bone to heal with greater bone density and size. This second mechanism affected both bone cell and bone matrix.

Bone is composed of collagen and calcium phosphate. The calcium phosphate forms crystalline hydroxyapatite. When the bone matrix is strained, the crystalline hydroxyapatite is strained and through its piezoelectric properties creates current flow. Electrical current flow has been reported in bone when strained. Electronic bone healing stimulators that place electrodes in the bony wound or pulse electromagnetic fields through bone report that their mechanism of healing is cell recruitment driven due to the induced current flow in bone. This mechanical strain induced current flow is one of two mechanisms of enhanced bone healing activated with the implants that use this method of enhanced healing.

The second of two mechanisms is the effect of compression and increased environmental pressure on the bone forming cells within the compression region. Bone cells in intact healthy bone have been shown to respond to mechanical loading to build more and stronger bone. Applicant's unexpected observation is that this response occurred in healing bone, which is a much different process than the remodeling that strengthens intact healthy bone. Bone healing includes inflammation, bone resorbtion, non-mineralized matrix formation, and mineralization of the matrix. Remodeling of intact bone does not include all of these processes. Implants designed to change shape to pull together and compress a healing bone fracture, cut or fusion is a significant advance in skeletal healthcare.

In general, the bone healing method and devices that change shape and pull together and compress bone can be applied throughout the skeletal system. For example, the invention can be an implant device for healing of fingers and toe bones. The method and devices provide the clinician the ability to implant the devices in their proper position and then release the device so that it can have the mechanical energy to (a) compress the bone segments, and (b) maintain the compression during the bone healing process. Accordingly, the devices have an activator that can be withdrawn from the device (such as, for example, a rod that can be withdrawn allowing a spring to provide the mechanical energy) or can remain with the device (such as, for example, a screw that can be rotated to allow a spring to provide the mechanical energy). Because the bone healing device is not activated until after it is in place, this allows the clinician to fully position it before activation. Moreover, when the device is not properly positioned, the bone healing device can be removed by the clinician before activation and then correctly positioned.

Furthermore, the implants can act as a scaffolding for bone thus conducting bone formation through the implant. This further facilitates the healing of bone segments.

The embodiments of the present inventions thus overcome the deficiencies of the prior rigid bone fixation implants, such as (1) not closing a gap formed at the edges of the fracture or cut due to inflammation, (2) holding the bone ends at a distance that is too far for bone cells to bridge to facilitate healing, (3) holding the bone so that compression loads in bone do not occur, (4) holding a gap between the ends of bone so that soft tissue can infiltrate into the gap and delay or prevent healing, (5) not mechanically straining bone to illicit piezoelectric current flow, (6) not mechanically straining or modulating bone cell pressure to stimulate these cells to form and model bone, (7) providing a scaffolding to conduct bone to grow through the implant and (8) others deficiencies that will become more clear in the review of the embodiments of the subject invention.

Moreover, the implants allow the clinician the ability to implant the devices in their proper position and then activate them. This combination significantly eases the burdens on the clinicians when using implants. Moreover, by doing so, this increases the clinicians' ability to properly place the implants. Proper placement is additionally beneficial as the implants can be utilized for scaffolding for bone growth.

In embodiments of the invention, the implant can include a shape memory metal (such as nitinol), which can utilize the pseudo elastic properties of such materials. Alternatively, the implant can be made of any elastic biocompatible metal (such as stainless steel, titanium, etc.) or can be made of an elastic biocompatible polymer (such as polyether ether ketone (PEEK),), polyethylene, etc.).

FIGS. 1-4 are illustrative of how the present invention overcome the deficiencies of the prior rigid bone fixation implants. FIG. 1 illustrates a rigid bone fixation plate and screw system of the prior art. This system includes a rigid bone plate 30 and rigid bone plate screws 40. As illustrated in FIG. 1, this system is utilized to hold in contact a first bone segment 10 and a second bone segment 20 at the bone healing junction 50 between these two bone segments.

Figure 2:
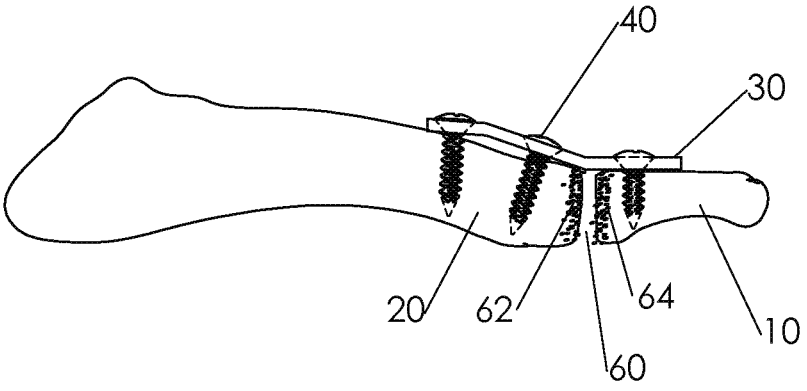
FIG. 2 illustrates the rigid bone fixation plate and screw system of FIG. 1 holding the bone segments apart.

FIG. 2 illustrates the rigid bone fixation plate and screw system of FIG. 1 holding first bone segment 10 and second bone segment 20 apart after formation of an inflammation, motion or procedure induced gap 60 between the bone healing interface 62 (of second bone segment 20) and bone healing interface 64 (of first bone segment 10).

Figure 3:
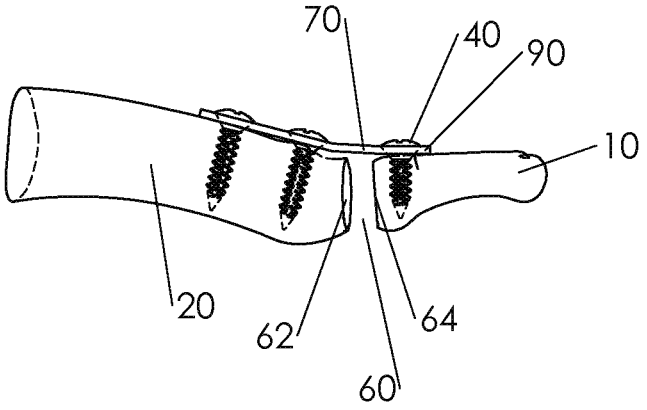
FIG. 3 illustrates a shape changing bone plate with displacement section extended, unstable, and able to pull together and compress bone segments so as to close the gap and compress the bone segments at the healing interfaces.
Figure 4:
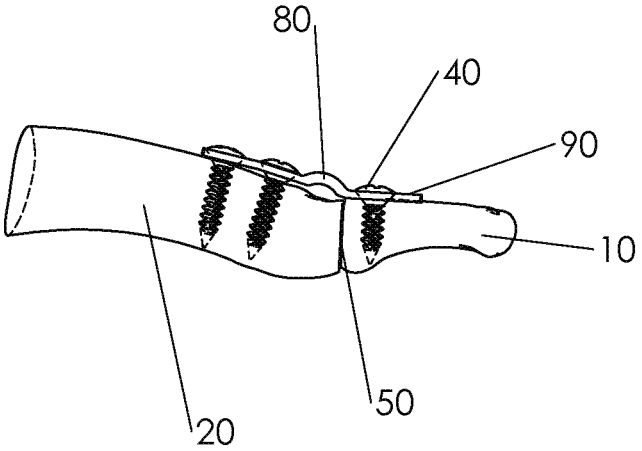
FIG. 4 illustrates the shape changing bone plate with displacement section of FIG. 3 contracted to hold the gap closed and compress the bone segments.

In embodiments of the present invention shown in FIGS. 3-4, a shape changing plate 90 utilizes a shape changing section 70 between first bone segment 10 and second bone segment 20 that can deform to become section 80 and pull so the fragments together so as to close the bony gap 60 and hold the bone healing interfaces 62 and 64 in contact. The activator is not shown in FIGS. 3-4.

Figure 5:
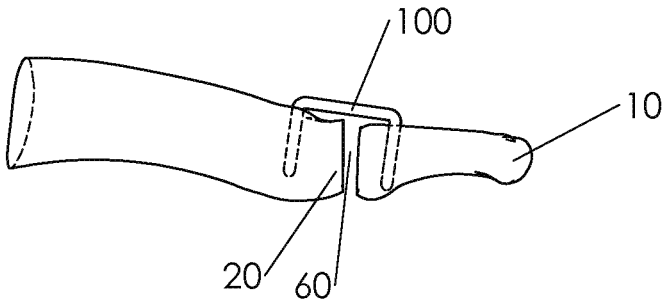
FIG. 5 illustrates a shape changing bone staple with the bridge extended, legs straightened, and mechanically unstable so that its spontaneous shape change closes the gap.
Figure 6:
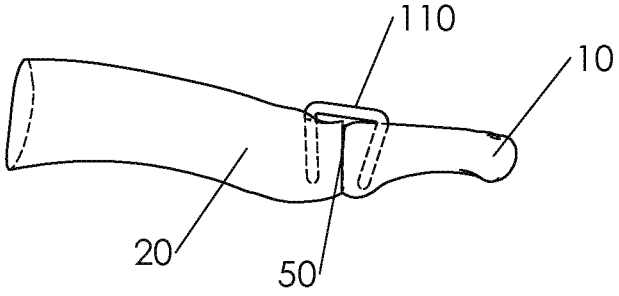
FIG. 6 illustrates the shape changing bone staple of FIG. 5 with the bridge contracted and legs deflected inward to hold the gap closed and compress the bone segments.

FIGS. 5-6 are illustrative of a shape changing bone staple. Such shape changing bone staple does not include an activator. FIG. 5 illustrates a shape changing bone staple 100 with the bridge extended, legs straightened and mechanically unstable so that its spontaneous shape change can close the gap 60. FIG. 6 illustrates the shape changing bone staple 100 of FIG. 5 with the bridge contracted and legs deflected inward to hold the gap 50 closed and compress the bone segments 10 and 20. The contracted shape changing bone staple 100 of FIG. 5 is shape changing bone staple 110 of FIG. 6.

Accordingly, the shape changing staple 100 (in its uncontracted state) can shorten its bridge and swings its legs inward its contract to close the gap 60 and hold the healing interface 50 in contact. The shape changing bridge and legs of staple 100 act together to pull together and compress the bone segments to avoid bone gaping and strain the healing bone.

Shape Changing Cage (with Internal Spring)

FIGS. 7-12 are illustrative of a shape changing cage used to pull together and compress bone segments. This is an example of a bone healing implant that can be positioned by the clinician while the implant does not apply mechanical force to compress the bone segments (to be healed) and, after positioning, the bone healing implant can be mechanically activated to apply the compressive mechanical force.

Figure 7:
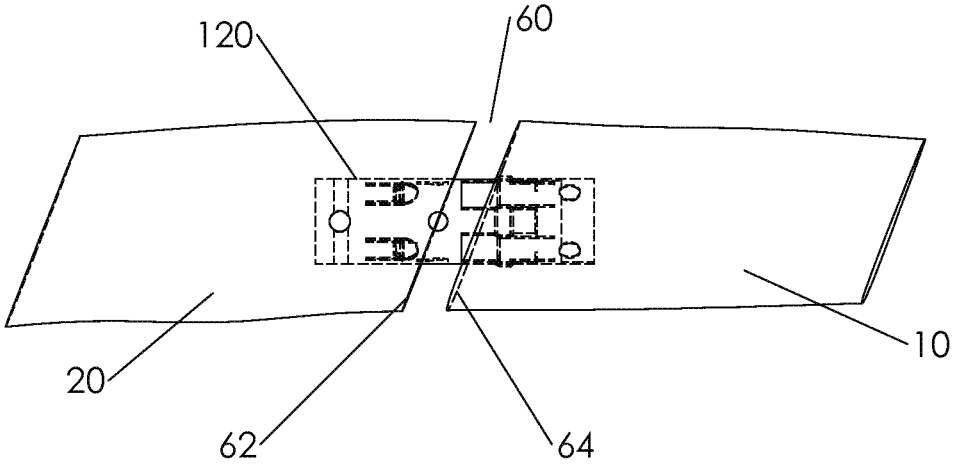
FIG. 7 illustrate a shape changing cylindrical fenestrated hollow cage, in its extended length, contracted diameter and unstable state, which uses an internal spring to close the gap and compress the bone interfaces.

FIG. 7 illustrates a shape changing cylindrical fenestrated hollow cage 120, in its extended length, contracted diameter and unstable state, which uses an internal spring to close the gap 60 and compress the bone interfaces 62 and 64.

Figure 8:
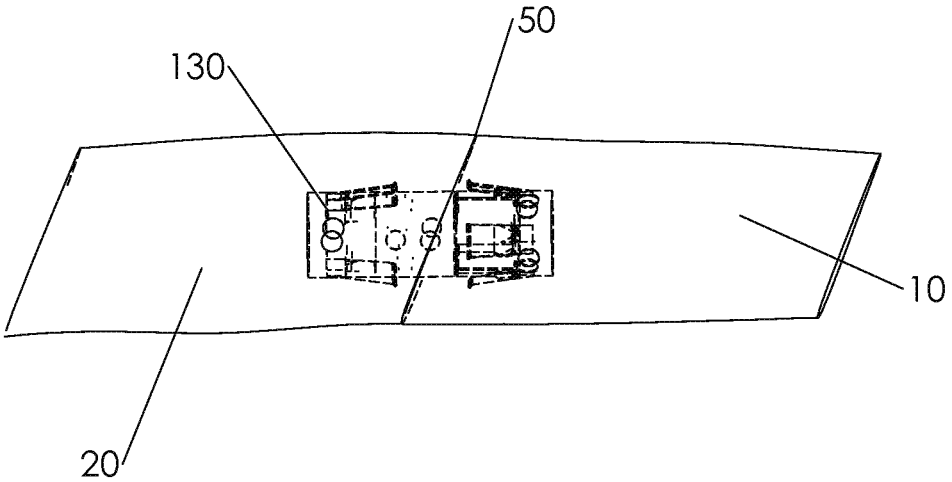
FIG. 8 illustrates the shape changing cylindrical fenestrated hollow cage of FIG. 7 in its contracted length and expanded diameter using the internal spring's strain energy to expand the cage diameter, lock into the central lumen of bone and shorten the cage's length so as to closed and compress the gap between bone segment and interfaces.

FIG. 8 illustrates the shape changing cylindrical fenestrated hollow cage 120 of FIG. 7 in its contracted length and expanded diameter (shape changing cylindrical fenestrated hollow cage 130) using an internal spring's strain energy to expand the cage diameter, lock into the central lumen of bone and shorten the length of cage shape changing cylindrical fenestrated hollow cage 130 (as compared to shape changing cylindrical fenestrated hollow cage 120) so as to closed and compress the gap 50 between bone segments 10 and 20.

Figure 9:
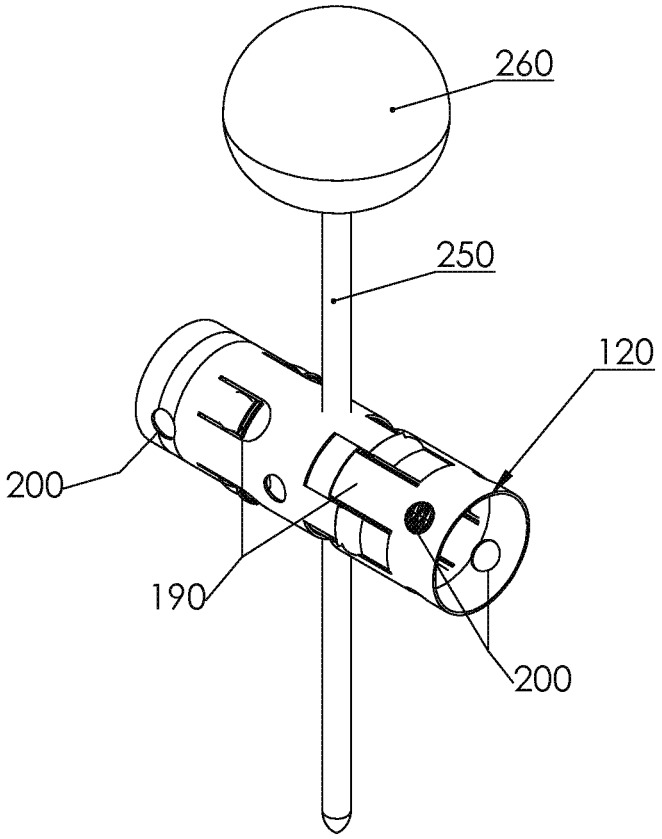
FIG. 9 illustrates an orthogonal view of the bone fixation cylindrical cage of FIG. 7 with lock pin in its elongated and diametrically contracted pre-implantation condition with maximum stored mechanical strain energy.

FIG. 9 illustrates an orthogonal view of the bone fixation cylindrical cage 120 of FIG. 7 with lock pin 250 in its elongated and diametrically contracted pre-implantation condition with maximum stored mechanical strain energy. Lock pin 250 includes lock pin manipulator 260. FIG. 9 further shows the movable connected expansion members 190 and the circular fenestrations 200 (for bone growth) of bone fixation cylindrical cage 120.

Figure 10:
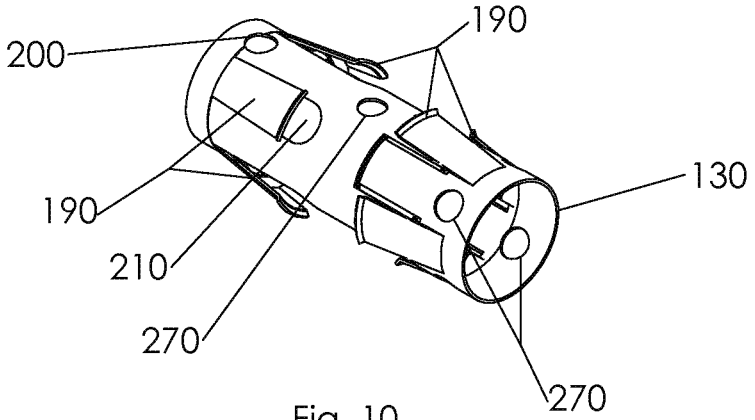
FIG. 10 illustrates an orthogonal view of the bone fixation cylindrical cage of FIG. 8 in its shortened and expanded post-implantation condition with no stored mechanical strain energy.

FIG. 10 illustrates an orthogonal view of the bone fixation cylindrical cage 130 of FIG. 8 in its shortened and expanded post-implantation condition with no stored mechanical strain energy. (When utilized, the bone fixation cylindrical cage does not fully shorten, so some of the stored mechanical strain energy remains to maintain compression.) FIG. 10 shows the movable connected expansion members 190 (after movement) and the circular fenestrations 200 of bone fixation cylindrical cage 130. FIG. 10 also shows elongated fenestrations for bone growth 210 and lock pin receiver 270.

Figure 11:
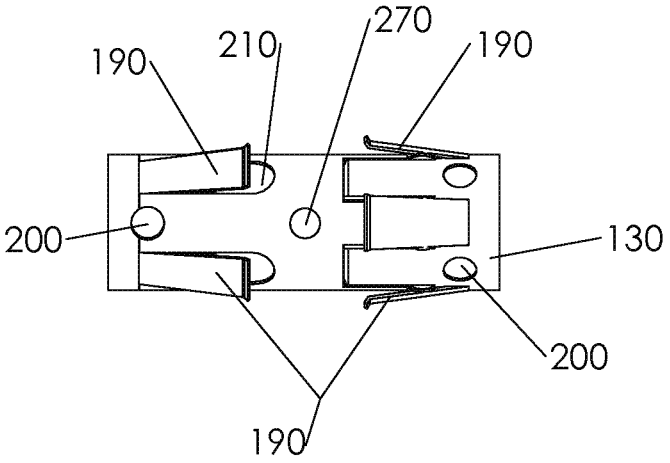
FIG. 11 illustrates a plane view of a bone fixation cylindrical cage of the bone fixation cylindrical cage of FIG. 8 in its shortened and expanded post-implantation condition with no stored mechanical strain energy showing bone locking members, bone in growth fenestrations, circular fenestrations, and lock pin receiver.

FIG. 11 illustrates a plane view of the bone fixation cylindrical cage 130 of FIG. 8 in its shortened and expanded post-implantation condition with no stored mechanical strain energy showing bone locking members 190, bone in growth fenestrations 210, circular fenestrations 200, and lock pin receiver 270.

Figure 12:
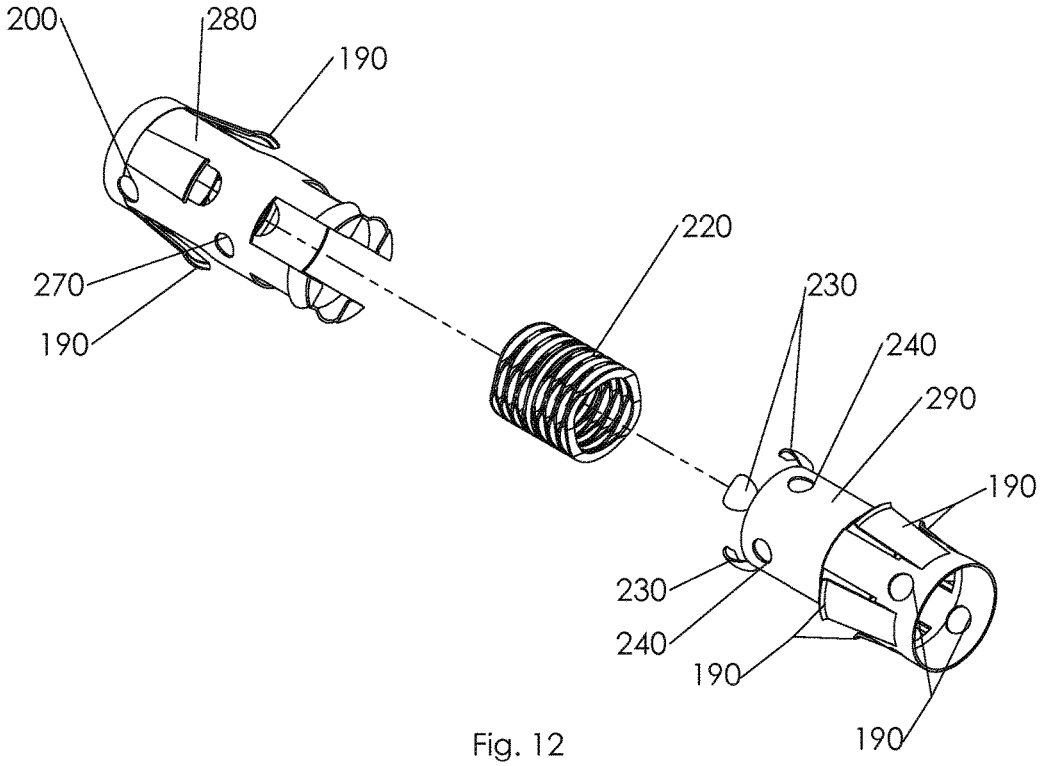
FIG. 12 illustrates an orthogonal view of the components of the bone fixation cylindrical cage of FIGS. 7-8 that is disassembled to show the two cylindrical components and spring.

FIG. 12 illustrates an orthogonal view of the components of the bone fixation cylindrical cage of FIGS. 7-8 that disassembled to show its two cylindrical components 280 and 290 and spring 220. FIG. 12 also shows the movably connected expansion member actuator 230 and the shape changing cylindrical internal locking fenestration 240.

During use, the shape changing cylindrical fenestrated hollow cage 120 is inserted in its extended length and contracted diameter. Once properly positioned by the clinician, the shape changing cage 120 is activated so that it takes on a shortened and diametrically expanded configuration of shape changing cage 130. In the illustrated embodiment, activation is accomplished by pulling the mechanism lock pin 250 by its manipulator 260 to remove it from the shape changing cage. Once activated the spring 220 elongates to pull together the cage components 280 and 290. As the cage components over slide one another the locking member actuators 230 push out on the expansion member 190 to lock into the lumen of bone and pull the two bone segments 10 and 20 together and hold and compress their healing interface. The cage's fenestrations and lumens act to conduct bone to form within the lumen and across the healing site.

It should be noted that in this design, the lock pin 250 is utilized to keep the shape changing cylindrical fenestrated hollow cage 120 in its extended length and, once the lock pin 250 is withdrawn the spring 220 acts on the shape changing cylindrical fenestrated hollow cage 120 to transition to the shortened and diametrically expanded configuration of shape changing cage 130 due to mechanical properties of the spring 220 and cage materials used.

For example, the materials used in fabricating the shape changing cage 120 can include nitinol, and the spring 220 maintains nitinol in the shape changing cage 120 in the form of stress induced or stress retained martensite. When the spring 220 is released, some or all of the nitinol in the form of martensite changes in form to the form of austenite. Stress induced martensite is created when nitinol in its austenitic crystalline structure is strained. Stress retained martensite is created by cooling austenitic nitinol below its martensitic finish temperature, manipulating the device to a second shape and then mechanically straining the device into this second shape and restraining it with a mechanical activator so that at higher temperatures its martensitic structure is retained until the implant is activated. Alternatively, the materials used in shape changing cage 120 can include a different shape memory metal or can include only metal that is not a shape memory metal. With respect to the later, the shape changing cage 120 would be held in a different shape without exceeding the elastic deformation limits of the metal utilized.

In such embodiments described above, the spring 220 is exerting effort to extend and is not used to apply compressive forces. In other embodiments, a spring can be used to provide compressive forces; however, such design is viewed as being less stable (and less advantageous) because the tension in the spring can be compromised over time.

Shape Changing Cage (without Internal Spring)

FIGS. 13-18 are illustrative of a shape changing cage used to pull together and compress bone segments. This is another example of a bone healing implant that can be positioned by the clinician while the implant does not apply mechanical force to compress the bone segments (to be healed) and, after positioning, the bone healing implant can be mechanically activated to apply the compressive mechanical force. Unlike the shape changing cage of FIGS. 7-12, this shape changing cage does not utilize an internal spring.

Figure 13:
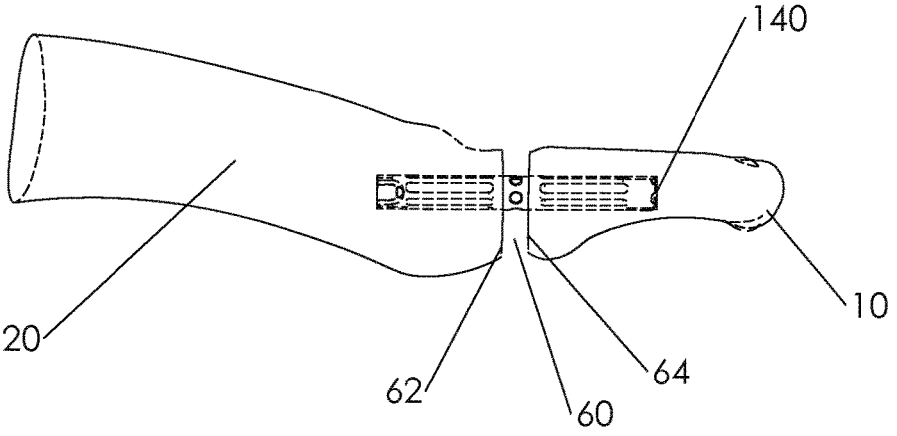
FIG. 13 illustrates a shape changing cylindrical fenestrated hollow cage in its extended length, contracted diameter, and unstable state that uses its elastic material properties to close the gap and compress the bone interfaces.

FIG. 13 illustrates a shape changing cylindrical fenestrated hollow cage 140 in its extended length, contracted diameter and unstable state that uses its elastic material properties to close the gap 60 and compressing the bone interfaces 62 and 64.

Figure 14:
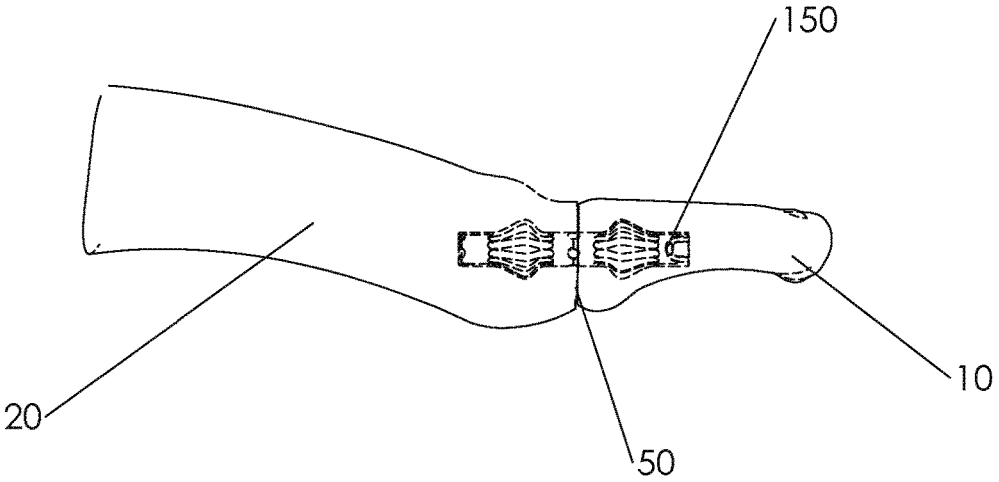
FIG. 14 illustrates the shape changing cylindrical fenestrated hollow cylinder of FIG. 13 in its contracted length and expanded diameter using its material properties to pull the gap closed and compress the bone interfaces.

FIG. 14 illustrates the shape changing cylindrical fenestrated hollow cylinder 140 of FIG. 13 in its contracted length and expanded diameter (shape cylindrical fenestrated hollow cylinder 150) using its material properties to pull the gap 50 closed and compress the bone interfaces 62 and 64.

FIG. 15 illustrates the orthogonal view of a bone fixation cylindrical cage 140 of FIG. 13 in its elongated and diametrically contracted pre-implantation condition with bone ingrowth fenestrations 520 and holes 510, and elongated ribs 570 storing maximum mechanical strain energy. FIG. 15 further shows instrument driving fenestrations 540, instrument release fenestrations 550, and shape changing bone fixation cylinder lumen 560 (for bone ingrowth).

FIG. 16 illustrates the orthogonal view of a bone fixation cylindrical cage 150 of FIG. 14 in its shortened and expanded post-implantation condition with bulging ribs 530 and no stored mechanical strain energy.

Figure 17:
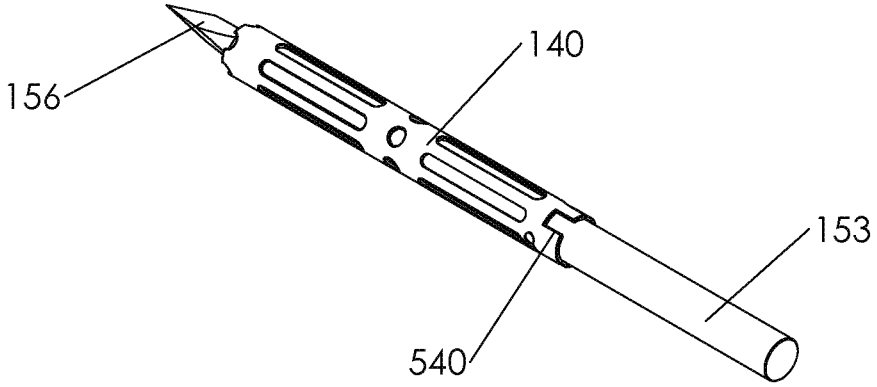
FIG. 17 illustrates an orthogonal view of the bone fixation cylindrical cage of FIG. 13 in its extended and diametrically contracted pre-implantation state while locked on an implantation mandrel having a bone cutting insertion tip, with the mandrel lobe engaged in cage instrument fenestration and the driver fenestrations accessible to facilitate release.

FIG. 17 illustrates the orthogonal view of the bone fixation cylindrical cage 140 of FIG. 13 in its extended and diametrically contracted pre-implantation state while locked on the implantation mandrel 153 having a bone cutting insertion tip 156, with the mandrel lobe 155 engaged in cage instrument fenestration 550 and the driver fenestrations 540 accessible to facilitate release. (The mandrel lobe 155 is shown in FIG. 18).

Figure 18:
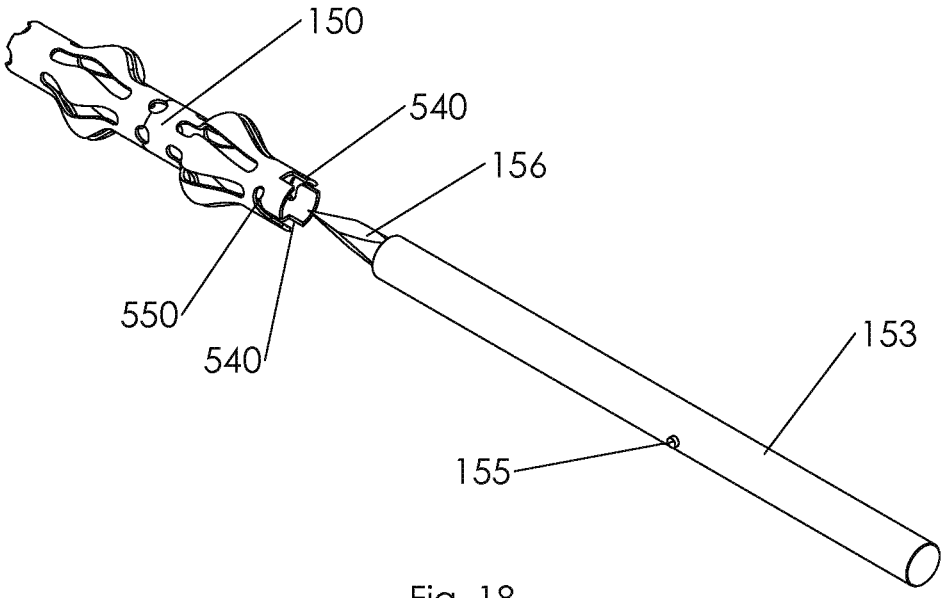
FIG. 18 illustrates an orthogonal view of the bone fixation cylindrical cage of FIG. 14 in its shortened and expanded post-implantation configuration following release from the implantation mandrel through release of the mandrel lobe and cage instrument release fenestration.

FIG. 18 illustrates an orthogonal view of the bone fixation cylindrical cage 150 in its shortened and expanded post-implantation configuration following release from the implantation mandrel 153 through release of the mandrel lobe 155 and cage instrument release fenestration 550.

During use, the shape changing cage 140 is inserted while in its extended length and contracted diameter by the use of the insertion mandrel 153. The mandrel 153 is sharp with a cutting tip 156 on one end and is advanced into bone while turning. Once inserted in bone, the shape changing cage 140 is released and takes on a shortened and diametrically expanded configuration (of shape changing cage 150). To release, the cage 140 and mandrel 153 are counter rotated so as to unlock the cage 140 from the mandrel 153. The diameter expansion locks the cage into bone, the shortening brings the bones together and compresses, the fenestrations and lumen conduct bone through the cage and across the healing interface.

Shape Changing Washer and Bone Screw System

FIGS. 19-25 are illustrative of a shape changing washer and bone screw system used to pull together and compress bone segments. This is an example of a bone healing implant in which compressive mechanical force is applied while the implant is being positioned by the clinician. This embodiment is unique in that it uses elastic and pseudo-elastic deformation of the shape changing washer to implement and maintain the compressive forces.

Figure 19:
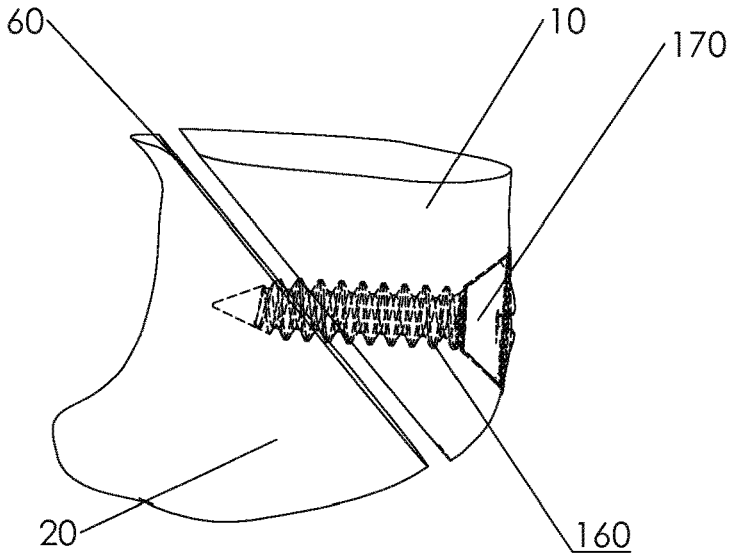
FIG. 19 illustrates a shape changing washer it its unstable state that, using the material's elastic properties, pulls on a bone screw to pull together bone segments to close the gap.

FIG. 19 illustrates a shape changing washer 170 it its unstable state that, using the material's elastic properties, pulls on a bone screw 160 to pull together bone segments 10 and 20 to close the gap 60.

Figure 20:
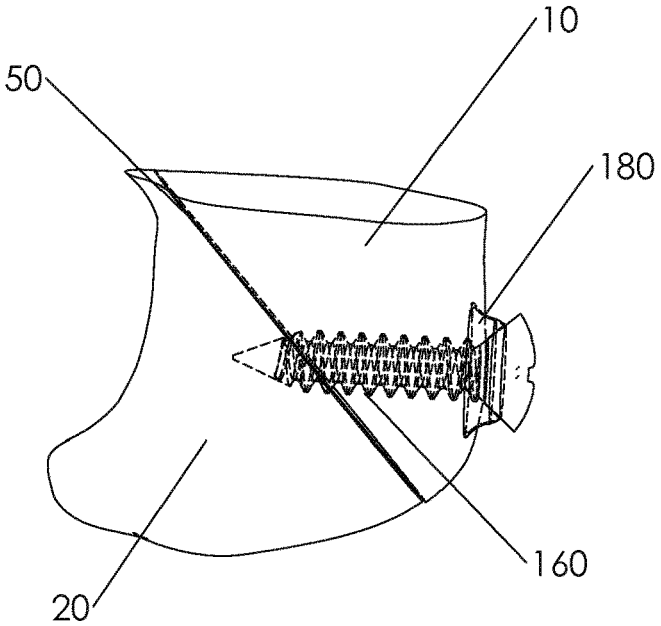
FIG. 20 illustrates the changing washer of FIG. 19 that, using the material's elastic properties, deflects its structure to pull on a bone screw to pull together bone segments, hold the gap closed, and compress the bone segments at the healing interface.

FIG. 20 illustrates the shape changing washer 170 of FIG. 19 that, using the material's elastic properties, deflects its structure (shape changing washer 180) to pull on the bone screw 160 to pull together bone segments 10 and 20, hold the gap 50 closed, and compress the bone segments 10 and 20 at the healing interface.

Figure 21:
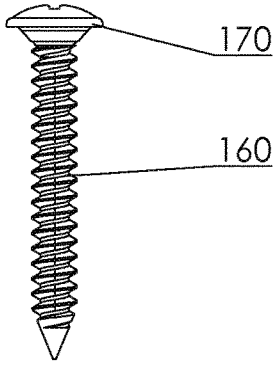
FIG. 21 illustrates a threaded bone screw with mechanical energy storing shape changing washer of fully strained and storing maximum energy.
Figure 22:
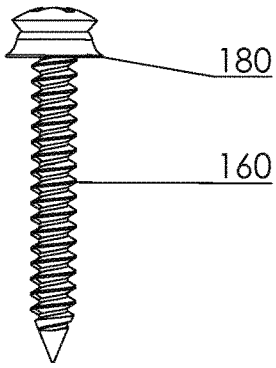
FIG. 22 illustrates the threaded bone screw and mechanical energy shape changing washer of FIG. 21 with the mechanical energy storing shape changing washer partially strained and storing an intermediate amount of energy.
Figure 23:
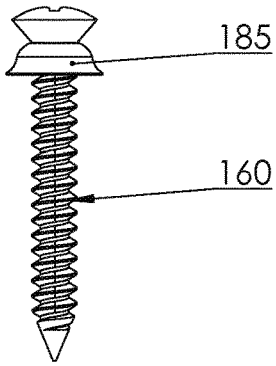
FIG. 23 illustrates the threaded bone screw and mechanical energy storing shape changing washer of FIG. 21 with the mechanical energy storing shape changing washer fully recovered in its shape and storing no energy.

FIGS. 21-23 illustrate the shape changing of the shape changing washer 170 as it is utilized with threaded bone screw 160. FIG. 21 illustrates threaded bone screw 160 with mechanical energy storing shape changing washer 170 fully strained and storing maximum energy. FIG. 22 illustrates the threaded bone screw 160 and mechanical energy storing shape changing washer 170 of FIG. 21 partially strained (mechanical energy storing shape changing washer 180) and storing an intermediate amount of energy. FIG. 23 illustrates the threaded bone screw 160 and mechanical energy storing shape changing washer 170 of FIG. 21 fully recovered in its shape (mechanical energy storing shape changing washer 185) and storing no energy.

Figure 24:
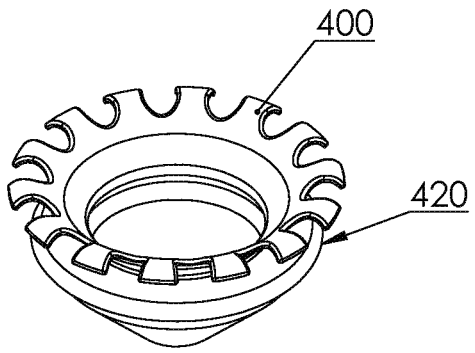
FIG. 24 illustrates an orthogonal view of an alternate embodiment of a shape changing washer that can be used with a threaded bone screw, showing the shape changing washer fully recovered in its shape changing bellows section and storing no energy.
Figure 25:
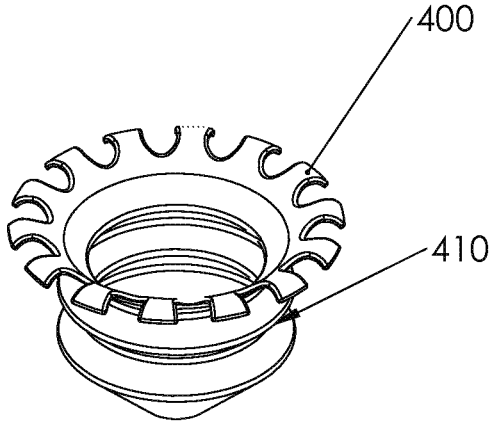
FIG. 25 illustrates an orthogonal view of the alternate embodiment of the shape changing washer of FIG. 24 showing the shape changing washer fully extended in its shape changing bellows section and storing maximum energy.

FIGS. 24-25 illustrate orthogonal views of an alternate embodiment of a shape changing washer 400 that can be used with a threaded bone screw (such as threaded bone screw 160 shown in FIGS. 21-23). In FIG. 24, shape changing washer 400 is shown fully recovered in its shape changing bellows section 420 and storing no energy. In FIG. 25, shape changing washer 400 is shown fully extended in its shape changing bellows section 410 and storing maximum energy.

During use, the shape changing washer 170 converts its elastic mechanical energy to pull the screw 160 by deflecting to a second shape (shape changing washer 180). The shape changing washer 185 (having no stored elastic energy) is on screw 160. As the screw 160 is threaded into bone, the shape changing washer 185 is strained and conforms to the screw 160 and takes on the strained shape (shape changing washer 170). If a gap forms, the shape changing washer 170 transitions to the partially deflected stated (shape changing washer 180) and pulls the screw 160 to hold the gap 60 closed so that the interface 50 is in constant contact and compressed.

In an alternate embodiment (shown in FIGS. 24-25), shape changing washer 400 has a bellows section that elongates and contracts to pull the bone screw 160. Fenestrations can be placed in the walls of the washer 400 to facilitate bone ingrowth and retention.

CONCLUSIONS AND SCOPE

The embodiments illustrated in this application are a significant advancement over the prior art rigid bone fixation implants in light of: (1) the simultaneous method of fixating bone and promoting healing, (2) the method of pulling together healing bone segments to that a gap does not form, (3) the method of minimizing non-healing due to fibrous tissue infiltration by blocking infiltration by not allowing a gap to form, (4) the method of stimulating bone cells and matrix by mechanical compression, (5) the method of stimulating bone healing through deformation of the hydroxyapitite calcium phosphate bone crystals to create current flow and bone cell recruitment to the healing wound, (6) the method of bone ingrowth and conduction through the implant and across the healing interface and (7) the incorporation of shape changing features into implants including but not limited to screws, washers, cylinders, plates, staples, rods, and external fixation devices.

Although the description above contains many specificities, these should not be construed as limiting the scope of the embodiments but as merely providing illustrations of some of the presently preferred embodiments. Thus the scope of the embodiment should be determined by the appended claims and their legal equivalents, rather than by the examples given.

The disclosures of all patents, patent applications, and publications cited herein are hereby incorporated herein by reference in their entirety, to the extent that they provide exemplary, procedural, or other details supplementary to those set forth herein.

REFERENCES

References in the field of the present invention include: U.S. Pat. No. 5,882,351 (Fox) ("Fox '351 Patent").

U.S. Pat. No. 6,287,310 (Fox) ("Fox '310 Patent").
U.S. Pat. No. 7,240,677 (Fox) ("Fox '677 Patent").
U.S. Patent Appl. Serial No. 2008/0161808 (Fox) ("Fox '808 Application").
U.S. Patent Appl. Serial No. 2010/0063506 (Fox) ("Fox '506 Application").
U.S. Pat. No. 6,059,787 (Allen) ("Allen '787 Patent").
U.S. Pat. No. 6,348,054 (Allen) ("Allen '054 Patent").
U.S. Pat. No. 6,783,531 (Allen) ("Allen '531 Patent").
U.S. Pat. No. 5,779,707 (Bertolet) ("Bertolet '707 Patent").
U.S. Pat. No. 6,325,805 (Flot) ("Flot '805 Patent").
U.S. Pat. No. 6,323,461 (Flot) ("Flot '461 Patent").
U.S. Pat. No. 5,449,359 (Groiso) ("Groiso '359 Patent").
U.S. Pat. No. 5,853,414 (Groiso) ("Groiso '414 Patent").
U.S. Pat. No. 7,635,367 (Groiso) ("Groiso '367 Patent").
U.S. Pat. No. 5,067,957 (Jervis) ("Jervis '957 Patent").
U.S. Pat. No. 5,246,443 (Mai) ("Mai '443 Patent").
U.S. Pat. No. 5,474,557 (Mai) ("Mai '557 Patent").
U.S. Pat. No. 3,939,828 (Mohr) ("Mohr '828 Patent").
U.S. Pat. No. 6,325,805 (Ogilvie) ("Ogilvie '805 Patent").
U.S. Patent Appl. Serial No. 2007/0162026 (Tipirneni) ("Tipirneni '026 Application").
U.S. Patent Appl. Serial No. 2007/0260248 (Tipirneni) ("Tipirneni '248 Application").
U.S. Patent Appl. Serial No. 2008/0147127 (Tipirneni) ("Tipirneni '127 Application").
Chamay, A, Tschantz, P, "Mechanical Influences in Bone Remodeling. Experimental Research on Wolff's Law," J. Biomechanics, 1972, 5:173-180 ("Chama 1972").
Chao, E Y S, Inoue, N, "Biophysical Stimulation of Bone Fracture Repair, Regeneration and Remodelling," European Cells and Materials, 2003, 6:72-85 ("Chao 2003").
Robling, A G, Castillo, A B, Turner, C H, "Biomechanical and Molecular Regulation of Bone Remodeling," Annu. Rev. Biomed. Eng., 2006, 8:455-498 ("Robling 2006").
Rubin, C T, Lanyon, L E "Regulation of Bone Mass by Mechanical Strain Magnitude," Calcif. Tissue Int., 1985, 37:411-417 ("Rubin 1985").
Turner, C H, Burr D B, "Basic Biomechanical Measurements of Bone: A Tutorial," Bone, 1993, 14:595-608 ("Turner 1993").
Warden, S J, Turner, C H, "Mechanotransduction in cortical bone is most efficient at loading frequencies of 5-10 hz," Bone, 2004, 34:261-270 ("Warden 2004").
Product Sell Sheet [online], BioMedical Enterprises, Inc., 2012 (San Antonio, Tex.) [retrieved on 2012-10-04] ("BioMedical Enterprises's Product Sell Sheet"). Retrieved from the Internet <URL: www.bme-tx.com/resources/details/category/product-sell-sheets>.
OSStaple Brochure, BioMedical Enterprises, Inc., A108-076 (Rev B), 2010.
Memory Staple Brochure, Biopro, Inc. (Port Huron, Mich.), Brochure No. 17704, rev 2 ("Biopro's Memory Staple Brochure").
Memory Staple Brochure, Depuy Inc., 0612-00-584 (Rev. 1), 2006 ("Depuy's Memory Staple Brochure").
Easy Clip SI Brochure, MemoMetal Inc. USA (Memphis, Tenn.), ECLP10000—rev. D, 2009.
Charlotte Foot and Ankle Fixation System, Wright Medical Technology, Inc. (Arlington, Tenn.) 50 040-105-Rev. Apr. 6, 2005.
FDA Clearance To Market Letter K080649, for Pogo® screw of FxDevices (Boca Raton, Fla.), dated Nov. 25, 2008 ("FDA K080649 Clearance to Market Letter").

What is claimed is:

1. A bone healing method comprising the steps of:

(a) selecting a bone implant operable for pulling together a first bone segment and a second bone segment and operable for compressing the first bone segment and the second bone segment at a bone healing interface;

(b) positioning the bone implant in a position to pull the first bone segment and the second bone segment together and to compress the first bone segment and the second bone segment at the bone healing interface, wherein (i) during the step of positioning, the bone implant is locked in a first shape, (ii) during the step of positioning, the bone implant applies no mechanical force to pull the first bone segment and the second bone segment together, and (iii) during the step of positioning, the bone implant applies no mechanical force to compress the first bone segment and the second bone segment at the bone healing interface; and (c) after positioning of the bone implant, mechanically activating the bone implant by unlocking the bone implant and releasing the bone implant from the first shape to a second shape that is different from the first shape, wherein (i) the mechanically activated bone implant pulls together the first segment and the second bone segment, (ii) the mechanically activated bone implant compresses the first bone segment and the second bone segment at the bone healing interface, and (iii) the mechanically activated bone implant maintains the first bone segment and the second bone segment at the bone healing interface while the first bone segment and the second bone segment heal.

2. The bone healing method of claim 1, wherein the bone implant is selected from the group consisting of cages, wires, staples, plates, screws, rods, tubular structures, external fixation devices, and combinations thereof.

3. The bone healing method of claim 1, wherein the first shape is an expanded shape.

4. The bone healing method of claim 3, wherein the second shape is a contracted shape.

5. The bone healing method of claim 1, wherein change of the bone implant from the first shape to the second shape comprises a first shape change in a first direction and a second shape change in another direction, wherein (a) the first shape change and the second shape change are different;

(b) the first shape change is a shape expansion or contraction; and (c) the second shape change is a shape expansion or contraction.

6. The bone healing method of claim 1, wherein the change of the bone implant to the second shape is operable for (a) pulling together the first bone segment and the second bone segment, and (b) compressing the first bone segment and the second bone segment at the bone healing interface.

7. The bone healing method of claim 1, wherein the bone implant comprises nitinol.

8. The bone healing method of claim 7, wherein the bone implant comprises an activator, wherein (a) before the activator is removed from the bone implant, the activator retains the bone implant locked in the first shape in which at least some of the nitinol in the bone implant is in the form of stress induced or retained martensite, (b) the activator is removed from the bone implant during the step of mechanically activating the bone implant, and (c) after the activator is removed from the bone implant, the bone implant changes shape, wherein at least some of the nitinol in the bone implant changes in form to austenite.

9. The bone healing method of claim 1, wherein the bone healing implant comprise a material selected from the group consisting of shape memory metals, elastic biocompatible metals, elastic biocompatible polymers, and combinations thereof.

10. The bone healing method of claim 1, wherein the bone healing implant comprises a material selected from the group consisting of stainless steel, titanium, and combinations thereof.

11. The bone healing method of claim 1, wherein the bone healing implant comprises a material selected from the group consisting of polyether ether ketone (PEEK), polyethylene, and combinations thereof.

12. The bone healing method of claim 1, wherein (a) the bone implant comprises nitinol, and (b) before the mechanically activating the bone implant, the bone implant is in the form of martensite.

13. The bone healing method of claim 1, wherein the bone implant holds together the first bone segment and the second bone segment such that soft tissue infiltration is blocked.

14. The bone healing method of claim 1, wherein the bone implant deforms the first bone segment and the second bone segment so as to create an electrical current flow in the first bone segment and the second bone segment.

15. The bone healing method of claim 1, wherein the bone implant comprises a shape changing cage.

16. The bone healing method of claim 15, wherein the shape changing cage comprises at least one bone conducting scaffold feature.

17. The bone healing method of claim 15, wherein the shape changing cage comprises a first component and a second component.

18. The bone method of claim 17, wherein during the step of mechanical activation:

(a) a locking pin is removed from the bone implant; and (b) the first component and the second component are pulled together, wherein the pulling together of the first component and the second component (i) pulls together the first bone segment and the second bone segment, (ii) compresses the first bone segment and the second bone segment at the bone healing interface, and (iii) maintains the first bone segment and the second bone segment at the bone healing interface while the first bone segment and the second bone segment heal.

19. The bone healing method of claim 18, wherein the shape changing cage comprises nitinol.

20. The bone healing method of claim 18, wherein the shape changing cage comprises a material selected from the group consisting of shape memory metals, elastic biocompatible metals, elastic biocompatible polymers, and combinations thereof.

21. The bone healing method of claim 18, wherein the shape changing cage comprises a material selected from the group consisting of stainless steel, titanium, and combinations thereof.

22. The bone healing method of claim 18, wherein the shape changing cage comprises a material selected from the group consisting of polyether ether ketone (PEEK), polyethelene, and combinations thereof.

23. The bone healing method of claim 15, wherein the shape changing cage comprises:

(a) a first cylindrical component; and (b) a second cylindrical component, wherein the first cylindrical component and second cylindrical component are locked in place to prevent them from moving together.

24. The bone method of claim 15, wherein the bone implant further comprises a mandrel that locks the shape changing cage in ft the first shape.

25. The bone healing method of claim 24, wherein the mandrel comprises a bone cutting insertion tip that is used during the step of positioning the bone implant.

26. The method of claim 24, wherein the step of mechanically activating the bone implant comprises unlocking the cage by removing the mandrel from the implant, wherein (a) unlocking the cage allows the cage to change its shape; and (b) the change in shape of the cage (i) pulls together the first segment and the second bone segment, (ii) compresses the first bone segment and the second bone segment at the bone healing interface, and (iii) maintains the first bone segment and the second bone segment at the bone healing interface while the first bone segment and the second bone segment heal.

27. The bone healing method of claim 24, wherein the shape changing cage comprises nitinol.

28. The bone healing method of claim 24, wherein the shape changing cage comprises a material selected from the group consisting of shape memory metals, elastic biocompatible metals, elastic biocompatible polymers, and combinations thereof.

29. The bone healing method of claim 24, wherein the shape changing cage comprises a material selected from the group consisting of stainless steel, titanium, and combinations thereof.

30. The bone healing method of claim 24, wherein the shape changing cage comprises a material selected from the group consisting of polyether ether ketone (PEEK), polyethylene, and combinations thereof.

*31. A bone healing method comprising the steps of:*

*(a) selecting a bone implant, wherein the bone implant comprises at least one bone scaffold feature;*

*(b) positioning the bone implant in a position to pull a first bone segment and a second bone segment together and to compress the first bone segment and the second bone segment at a bone healing interface, wherein, during the step of positioning*

*(i) the bone implant is locked in a first shape,*

*(ii) the bone implant applies no mechanical force to pull the first bone segment and the second bone segment together, and*

*(iii) the bone implant applies no mechanical force to compress the first bone segment and the second bone segment at the bone healing interface; and*

*(c) after the bone implant is positioned, mechanically activating the bone implant by unlocking the bone implant and releasing the bone implant from the first shape to a second shape that is different from the first shape, wherein*

(*i*) *the bone implant pulls together the first bone segment and the second bone segment,*

(*i*) *the bone implant compresses the first bone segment and the second bone segment at the bone healing interface, and*

(*ii*) *the bone implant maintains the first bone segment and the second bone segment at the bone healing interface while the first bone segment and the second bone segment heal, wherein the bone scaffold feature conducts bone through the bone implant and across the healing bone interface while the first bone segment and the second bone segment heal.*

* * * * *